United States Patent
Kim

(10) Patent No.: US 10,888,591 B2
(45) Date of Patent: Jan. 12, 2021

(54) **NANO-VESICLES DERIVED FROM GENUS *MICROCOCCUS* BACTERIA AND USE THEREOF**

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

(*) Notice: Subject to any disclaimer, the term of this patent is extended or adjusted under 35 U.S.C. 154(b) by 0 days.

(21) Appl. No.: 16/563,720

(22) Filed: Sep. 6, 2019

(65) Prior Publication Data

US 2019/0388479 A1    Dec. 26, 2019

Related U.S. Application Data

(63) Continuation of application No. PCT/KR2019/002341, filed on Feb. 27, 2019.

(51) Int. Cl.
| | | |
|---|---|---|
| *A61K 35/741* | (2015.01) | |
| *A61K 35/74* | (2015.01) | |
| *A23L 33/135* | (2016.01) | |
| *C12Q 1/689* | (2018.01) | |
| *A61K 8/99* | (2017.01) | |
| *A61K 9/00* | (2006.01) | |
| *A61P 9/10* | (2006.01) | |
| *A61P 11/00* | (2006.01) | |
| *A61P 25/28* | (2006.01) | |
| *A61P 3/10* | (2006.01) | |

(52) U.S. Cl.
CPC ............ *A61K 35/74* (2013.01); *A23L 33/135* (2016.08); *A61K 8/99* (2013.01); *A61K 35/741* (2013.01); *C12Q 1/689* (2013.01); *A23V 2002/00* (2013.01); *A61K 9/0073* (2013.01); *A61P 3/10* (2018.01); *A61P 9/10* (2018.01); *A61P 11/00* (2018.01); *A61P 25/28* (2018.01); *C12Q 2600/112* (2013.01)

(58) Field of Classification Search
None
See application file for complete search history.

(56) References Cited

U.S. PATENT DOCUMENTS

2012/0192295 A1* 7/2012 Kim .................. G01N 33/5088
800/9

FOREIGN PATENT DOCUMENTS

| JP | 5313659 B2 | 10/2013 |
|---|---|---|
| KR | 10-2011-0025603 A | 3/2011 |
| KR | 10-2011-0038575 A | 4/2011 |
| KR | 10-2016-0073157 A | 6/2016 |
| KR | 10-2018-0006303 A | 1/2018 |
| KR | 10-2018-0018354 A | 2/2018 |

OTHER PUBLICATIONS

Ruhr et al. Antinnicrob. Agents Chemother. 27: 841-845, 1985.*

* cited by examiner

*Primary Examiner* — Sarvamangala Devi
(74) *Attorney, Agent, or Firm* — Vorys, Sater, Seymour & Pease LLP; Mih Suhn Koh

(57) ABSTRACT

Provided are vesicles derived from bacteria belonging to the genus *Micrococcus*, a composition and a use thereof, wherein the vesicles and the composition comprising the same may be effectively used for the development of a method of diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes.

6 Claims, 17 Drawing Sheets
Specification includes a Sequence Listing.

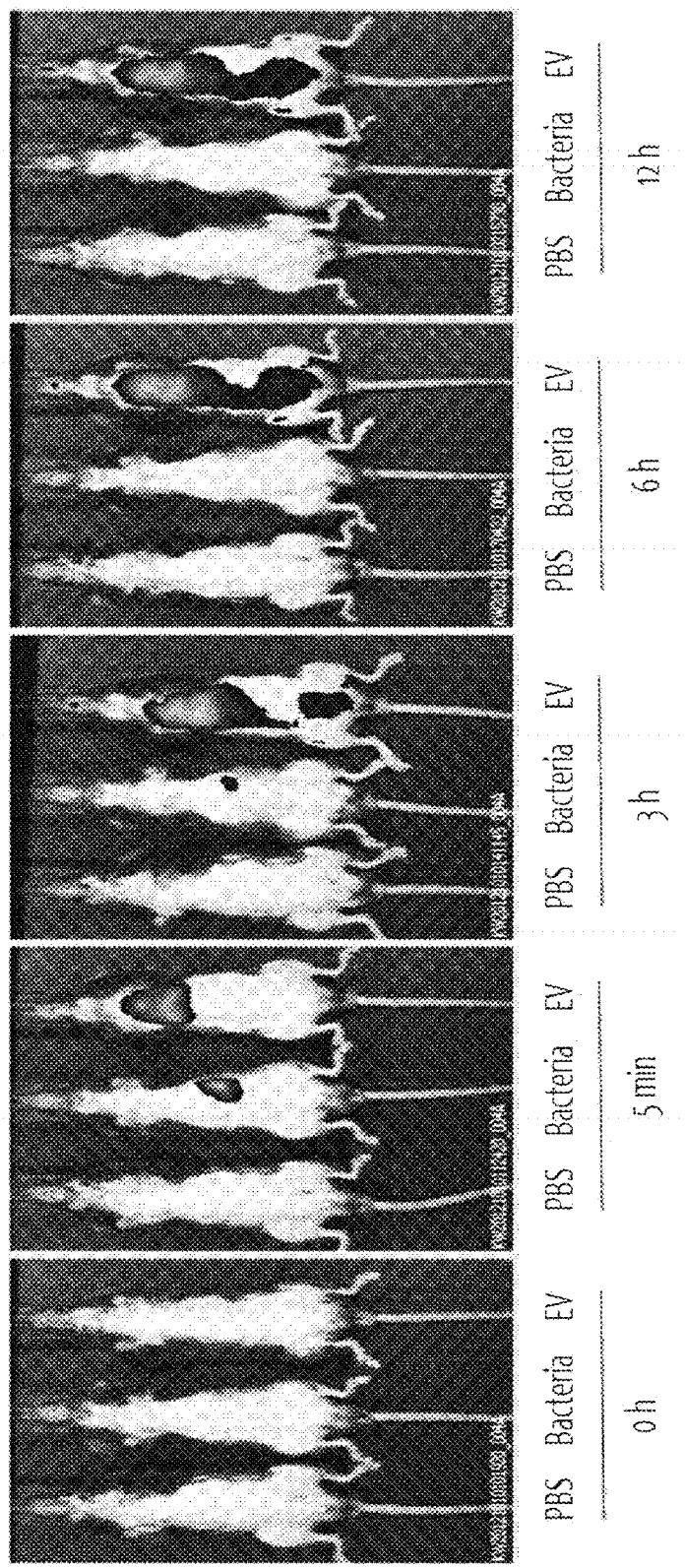

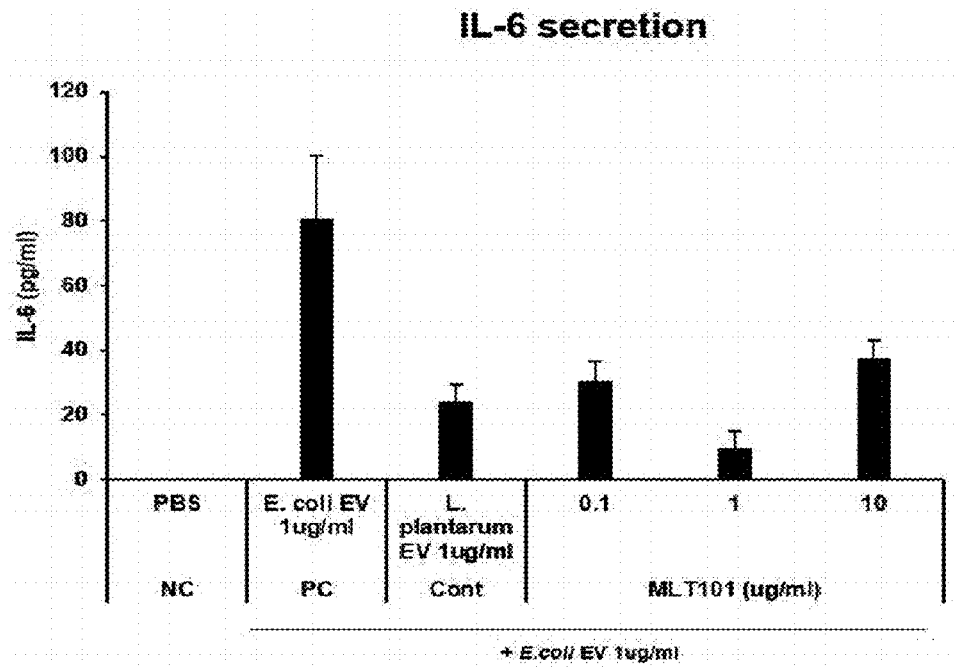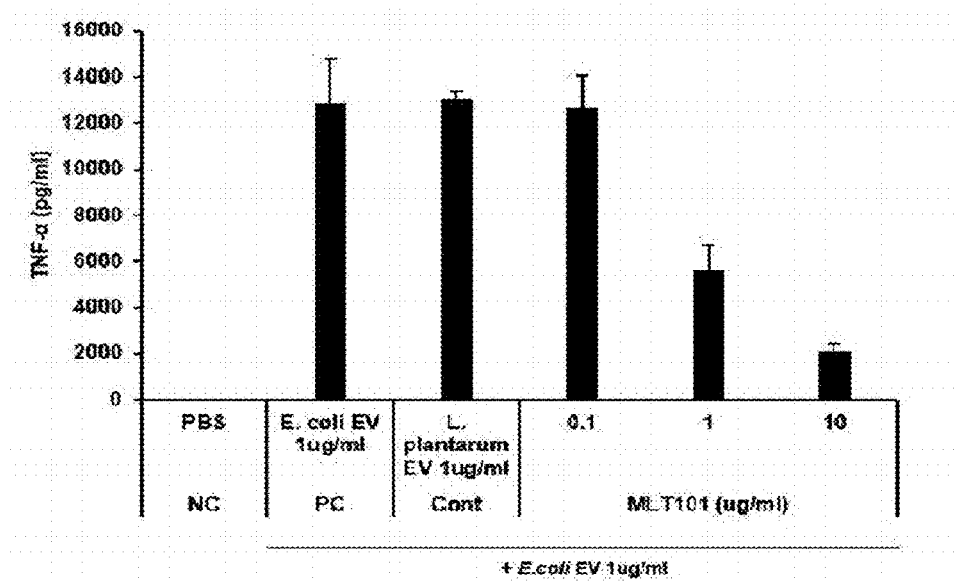

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)
<223> OTHER INFORMATION: a, c, g or t

<400> SEQUENCE: 1
tcgtcggcag cgtcagatgt gtataagaga cagcctacgg gnggcwgcag          50

<210> SEQ ID NO 2
<211> LENGTH: 55
<212> TYPE: DNA
<213> ORGANISM: Artificial Sequence
<220> FEATURE:
<223> OTHER INFORMATION: 16S_V4_R

<400> SEQUENCE: 2
gtctcgtggg ctcggagatg tgtataagag acaggactac hvgggtatct aatcc    55
```

NANO-VESICLES DERIVED FROM GENUS *MICROCOCCUS* BACTERIA AND USE THEREOF

CROSS-REFERENCE TO RELATED APPLICATION

This application is a Continuation Application of PCT/KR2019/002314, filed Feb. 27, 2019, which claims the benefit of priority from Korean Patent Application No. 10-2018-0024895, filed Feb. 28, 2018 and Korean Patent Application No. 10-2019-0022167, filed Feb. 26, 2019, the contents of each of which are incorporated herein by reference in its entirety.

SEQUENCE LISTING

The Sequence Listing submitted in text format (.txt) filed on Sep. 6, 2019, named "SequenceListing.txt", created on Sep. 6, 2019 (738 bytes), is incorporated herein by reference.

TECHNICAL FIELD

The present invention relates to nanovesicles derived from bacteria belonging to the genus *Micrococcus* and a use thereof, and more particularly, to a method of diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, and the like by using nanovesicles derived from bacteria belonging to the genus *Micrococcus*, and a composition for preventing, alleviating, or treating the disease which comprises the nanovesicles.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and the human lifespan. As an intractable chronic disease in the 21st century, cancer, cardiovascular diseases, chronic lung diseases, metabolic diseases, and neuropsychiatric diseases have become a big problem for public health in the country as main diseases that determine the human lifespan and the quality of life. These intractable chronic diseases are characterized by chronic inflammation accompanied by immune dysfunction due to causative factors.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. Bacteria-derived vesicles that are locally secreted from bacteria are absorbed via epithelial cells of the mucous membrane to thereby induce a local inflammatory response, and the vesicles having passed through the epithelial cells are systematically absorbed via lymphatic vessels and thereby distributed in respective organs, and immune and inflammatory responses are regulated in the organs in which the vesicles are distributed.

For example, vesicles derived from pathogenic Gram-negative bacteria such as *Escherichia coli* locally induce colitis, and promote systemic inflammatory responses and blood coagulation through vascular endothelial cell inflammatory responses when absorbed via the blood vessels. In addition, such vesicles are absorbed into muscle cells on which insulin acts, and the like to cause insulin resistance and diabetes. In contrast, vesicles derived from beneficial bacteria may regulate diseases by regulating immune functions and metabolic dysfunctions by pathogenic vesicles.

As immune response to factors such as bacteria-derived vesicles and the like, a Th17 immune response characterized by secretion of the interleukin (IL)-17 cytokine occurs where IL-6 is secreted when exposed to bacteria-derived vesicles, thus inducing the Th17 immune response. Inflammation by the Th17 immune response is characterized by neutrophil infiltration, and in a process where inflammation occurs, tumor necrosis factor-alpha (TNF-α), which is secreted from inflammatory cells such as macrophages, and the like, plays an important role in the development of a disease.

Bacteria belonging to the genus *Micrococcus*, which are Gram-positive bacteria belonging to the family Micrococcaceae, are widely distributed in nature such as water, dust, soil, and the like. Among these, *Micrococcus luteus* is known to produce riboflavin when grown in a toxic organic contaminant such as pyridine and absorb ultraviolet rays through the lutein pigment. It is also known that bacteria belonging to the genus *Micrococcus* are isolated from dairy products and beer and grown in dry or high-salt environments, and although not forming spores, the bacteria survive at a refrigeration temperature in a refrigerator for a long period of time. However, it has not yet been reported that bacteria belonging to the genus *Micrococcus* secrete vesicles extracellularly, and in particularly, there is no report of application thereof to the diagnosis and treatment of cancer, cardiovascular diseases, allergic/chronic pulmonary diseases, dementia, or metabolic diseases.

DISCLOSURE

Technical Problem

To address the above-described problems, as a result of having conducted intensive research, the inventors of the present invention confirmed through metagenomic analysis that the content of vesicles derived from bacteria belonging to the genus *Micrococcus* was significantly reduced in samples derived from patients with gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, compared to normal individuals. It was also confirmed that, when isolating vesicles from *Micrococcus luteus*, which is a bacterium belonging to the genus *Micrococcus* and treating macrophages therewith, the secretion of IL-6 and TNF-α by pathogenic vesicles was significantly inhibited, thus completing the present invention based on these findings.

Thus, an object of the present invention is to provide a method of providing information for diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes.

Further, another object of the present invention is to provide a composition for preventing, alleviating or treating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, comprising bacteria belonging to the genus *Micrococcus*-derived vesicles as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosis of gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, the method comprising the following steps:

(a) extracting DNAs from extracellular vesicles isolated a normal individual sample and a subject sample;

(b) performing polymerase chain reaction (PCR) on the extracted DNA using a pair of primers prepared based on a gene sequence present in 16S rDNA to obtain each PCR product; and (c) classifying a case in which a content of extracellular vesicles derived from bacteria belonging to the genus *Micrococcus* is lower than that of the normal individual sample, as gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, through quantitative analysis of the PCR product.

In addition, the present invention provides a method of diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, the method comprising the following steps:

(a) extracting DNAs from extracellular vesicles isolated a normal individual sample and a subject sample;

(b) performing polymerase chain reaction (PCR) on the extracted DNA using a pair of primers prepared based on a gene sequence present in 16S rDNA to obtain each PCR product; and (c) determining a case in which a content of extracellular vesicles derived from bacteria belonging to the genus *Micrococcus* is lower than that of the normal individual sample, as gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, through quantitative analysis of the PCR product.

As an exemplary embodiment of the present invention, the sample in Step (a) may be blood.

As another exemplary embodiment of the present invention, the primer pair in Step (b) may be primers of SEQ ID Nos. 1 and 2.

Further, the present invention provides a pharmaceutical composition for preventing or treating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, comprising vesicles derived from bacteria belonging to the genus *Micrococcus* as an active ingredient.

In one embodiment of the present invention, the pharmaceutical composition may comprise an ophthalmic composition.

In addition, the present invention provides a food composition for preventing or alleviating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, comprising vesicles derived from bacteria belonging to the genus *Micrococcus* as an active ingredient.

In addition, the present invention provides an inhalant composition for preventing or treating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, comprising vesicles derived from bacteria belonging to the genus *Micrococcus* as an active ingredient.

In addition, the present invention provides a cosmetic composition for preventing or alleviating atopic dermatitis, psoriasis, acne vulgaris, or hair loss, comprising vesicles derived from bacteria belonging to the genus *Micrococcus* as an active ingredient.

Furthermore, the present invention provides a method of preventing or treating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, the method comprising a step of administering a pharmaceutical composition comprising vesicles derived from bacteria belonging to the genus *Micrococcus* as an active ingredient to a subject.

Further, the present invention provides a use of vesicles derived from bacteria belonging to the genus *Micrococcus* for preventing or treating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes.

As an exemplary embodiment of the present invention, the vesicles may have an average diameter of 10 to 200 nm.

As another exemplary embodiment of the present invention, the vesicles may be secreted naturally or artificially from bacteria belonging to the genus *Micrococcus*.

As another exemplary embodiment of the present invention, the vesicles derived from bacteria belonging to the genus *Micrococcus* may be vesicles derived from *Micrococcus luteus*.

Advantageous Effects

The present inventors confirmed that intestinal bacteria are not absorbed into the body, but vesicles derived from bacteria are absorbed into the body through epithelial cells, systemically distributed, and excreted from the body through the kidneys, liver, and lungs, and that through a metagenomic analysis of vesicles derived from bacteria present in the blood of a patient, vesicles derived from bacteria belonging to a genus *Micrococcus* present in the blood of patients with gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, and diabetes had been significantly decreased as compared to those in normal individual. It was also confirmed that, when culturing *Micrococcus luteus*, which is a bacterium belonging to the genus *Micrococcus* in vitro and isolating vesicles therefrom, and then administering the isolated vesicles to inflammatory cells in vitro, the secretion of an inflammatory mediator by pathogenic vesicles was significantly inhibited, and thus it is anticipated that vesicles derived from bacteria belonging to the genus *Micrococcus* can be effectively used in a method of diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, and a composition for preventing, alleviating, or treating the above-described disease, and the like.

DESCRIPTION OF DRAWINGS

FIG. 1A is a series of photographs capturing distribution patterns of bacteria and vesicles derived from bacteria (EV) by time after the bacteria and the vesicles derived from bacteria were orally administered to mice.

FIG. 16 illustrates results of evaluating an effect of vesicles derived from *Micrococcus luteus* on the secretion of IL-6 and TNF-α, which are inflammatory mediators, by *E. coli* vesicles, after pretreatment of the vesicles prior to treatment with *E. coli* EVs, which are pathogenic vesicles, to evaluate an effect of vesicles derived from *Micrococcus luteus* on anti-inflammation and immune regulation.

BEST MODE

Figure 1B:
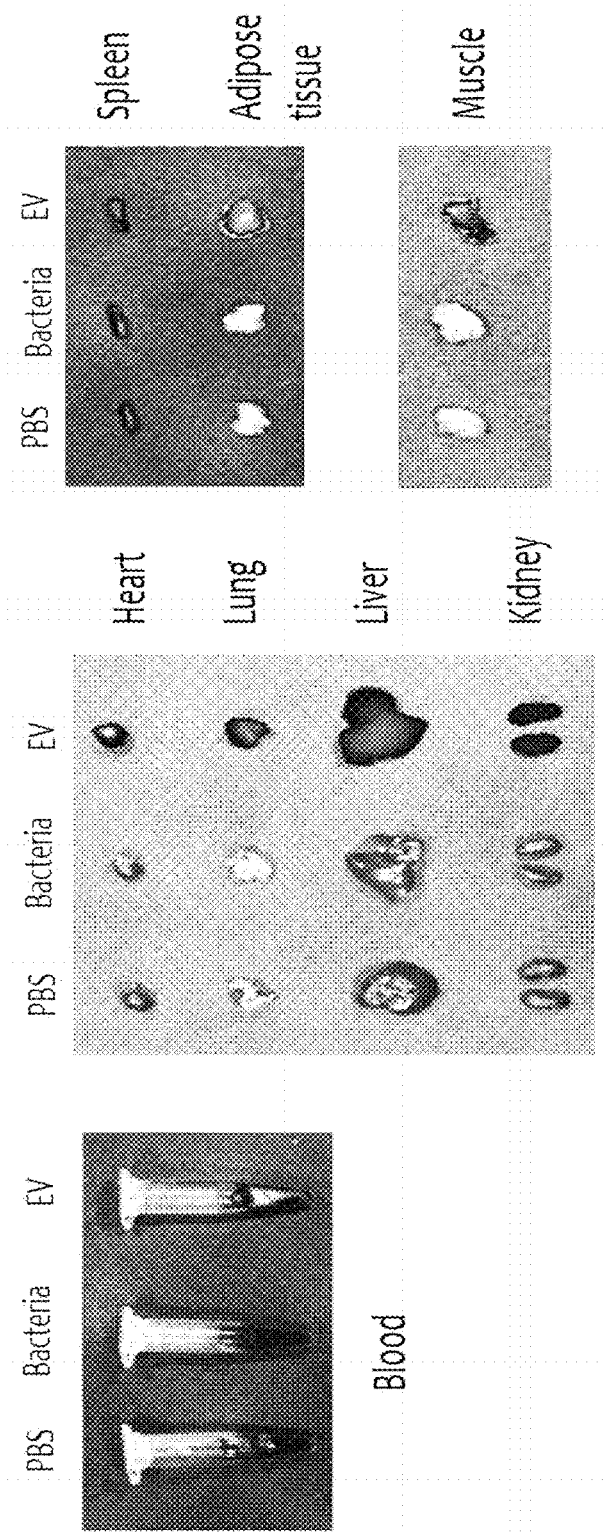
FIG. 1B is a result of evaluating the in vivo distribution patterns of the bacteria and the vesicles by harvesting blood, kidneys, liver, and various organs at 12 hours after orally administering the bacteria and the vesicles.

The present invention relates to vesicles derived from bacteria belonging to the genus *Micrococcus* and a use thereof.

The inventors of the present invention confirmed through metagenomic analysis that the content of vesicles derived from bacteria belonging to the genus *Micrococcus* was significantly reduced in clinical samples derived from patients with gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, and diabetes, compared to normal individual, through which it was confirmed that the diseases can be diagnosed. In addition, as a result of isolating vesicles from *Micrococcus luteus* and analyzing characteristics thereof, it was confirmed that the vesicles were able to be used as a composition for preventing, alleviating, or treating a disease such as gastric cancer, pancreatic cancer, cholangiocarcinoma, breast cancer, ovarian cancer, bladder cancer, myocardial infarction, cardiomyopathy, atrial fibrillation, variant angina, atopic dermatitis, macular degeneration, chronic obstructive pulmonary disease (COPD), dementia, and diabetes, and the like.

Thus, the present invention provides a method of providing information for diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, the method comprising the following steps:

(a) extracting DNAs from extracellular vesicles isolated a normal individual sample and a subject sample;

(b) performing polymerase chain reaction (PCR) on the extracted DNA using a pair of primers prepared based on a gene sequence present in 16S rDNA to obtain each PCR product; and (c) determining a case in which a content of extracellular vesicles derived from bacteria belonging to the genus *Micrococcus* is lower than that of the normal individual sample, as gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, and/or diabetes occur, the level of the disease, and the like.

The term "nanovesicle" or "vesicle" as used herein refers to a structure consisting of a nano-sized membrane secreted from various bacteria.

Vesicles derived from gram-negative bacteria or outer membrane vesicles (OMVs) have not only endotoxins (lipopolysaccharides) but also toxic proteins and bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from genus *Micrococcus* bacteria or produced artificially, are in the form of a sphere, and have an average diameter of 10 to 200 nm.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample may be blood, but is not limited thereto.

As another aspect of the present invention, the present invention provides a composition for preventing, treating, or alleviating gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, comprising vesicles derived from bacteria belonging to the genus *Micrococcus* as an active ingredient. The composition comprises a food composition, an inhalant composition, a cosmetic composition, and a pharmaceutical composition.

In addition, in the present invention, the food composition comprises a health functional food composition, and the pharmaceutical composition may comprise an ophthalmic composition, but the present invention is not limited thereto.

The term "prevention" as used herein refers to all actions that suppress gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, and/or diabetes, and the like or delay the onset thereof via administration of the composition according to the present invention.

The term "treatment" as used herein refers to all actions that alleviate or beneficially change symptoms of gastric cancer, pancreatic cancer, cholangiocarcinoma, breast cancer, ovarian cancer, bladder cancer, myocardial infarction, cardiomyopathy, atrial fibrillation, variant angina, atopic dermatitis, psoriasis, acne vulgaris, hair loss, macular degeneration, chronic obstructive pulmonary disease (COPD), dementia, or diabetes, and the like via administration of composition according to the present invention.

The term "alleviation" used as used herein refers to all actions that at least reduce a parameter associated with a condition to be treated, for example, the degree of symptoms.

The vesicles may be isolated from a culturing solution comprising bacteria belonging to the genus *Micrococcus* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be orally administered or may be parenterally administered (for example, administered intravenously, subcutaneously, intradermally, intranasally, or the intratracheally) according to the target method, and the administration dose may vary depending on the patient's condition and body weight, severity of disease, drug form, and administration route and period, but may be appropriately selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, the effective amount of the pharmaceutical composition according to the present invention may vary depending on the patient's age, sex, and body weight, and generally, 0.001 to 150 mg of the composition and preferably, 0.01 to 100 mg of the composition, per 1 kg of body weight, may be administered daily or every other day or may be administered once to three times a day. However, since the effective amount may be increased or decreased depending on the administration route, the severity of obesity, the gender, the body weight, the age, and the like, the administration dose is not intended to limit the scope of the present invention in any way.

In an inhalant composition of the present invention, the active ingredient may be directly added to an inhalant or may be used in combination with other ingredients, and may be appropriately used according to a general method. A mixing amount of the active ingredient may be appropriately determined according to the purpose of use thereof (for prevention or treatment).

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, stevia extract (for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art. The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

The cosmetic composition of the present invention may include not only vesicles derived from bacteria belonging to the genus *Micrococcus*, but also ingredients commonly used in cosmetic compositions, and may include, for example, general adjuvants such as an antioxidant, a stabilizer, a solubilizing agent, vitamins, pigments, and herbs, and a carrier.

In addition, the composition of the present invention may further include, in addition to the vesicles derived from bacteria belonging to the genus *Micrococcus*, a mixture of organic UV blocking agents that have long been used within a range that does not adversely affect a skin protective effect by reaction with vesicles derived from bacteria belonging to the genus *Micrococcus*. The organic UV blocking agent may be one or more selected from the group consisting of glyceryl PABA, drometrizole trisiloxane, drometrizole, digalloyl trioleate, disodium phenyl dibenzimidazole tetrasulfonate, diethylhexyl butamido triazone, diethylamino hydroxy benzoyl hexyl benzoate, DEA-methoxycinnamate, a mixture of lawsone and dihydroxyacetone, methylenebisbenzotriazolyltetramethylbutylphenol, 4-methylbenzylidene camphor, menthyl anthranilate, benzophenone-3(oxybenzone), benzophenone-4, benzophenone-8(dioxybenzone), butylmethoxydibenzoylmethane, bisethylhexyloxyphenolmethoxyphenyltriazine, cinoxate, ethyldihydroxypropyl PABA, octocrylene, ethylhexyldimethyl PABA, ethylhexylmethoxycinnamate, ethylhexyl salicylate, ethylhexyl triazone, isoamyl-p-methoxycinnamate, polysilicon-15(dimethicodiethylbenzal malonate), terephthalylidene dicamphor sulfonic acid and salts thereof, TEA-salicylate, and para-aminobenzoic acid (PABA).

Examples of products to which the cosmetic composition of the present invention may be added include cosmetics such as astringents, skin softeners, nourishing toners, various creams, essences, packs, foundations, and the like, cleansings, face cleansers, soaps, treatments, beauty liquids, and the like. Particular preparations of the cosmetic composition of the present invention include a skin lotion, a skin softener, a skin toner, an astringent, a lotion, a milk lotion, a moisturizing lotion, a nourishing lotion, a massage cream, a nourishing cream, a moisturizing cream, a hand cream, an essence, a nourishing essence, a pack, a soap, a shampoo, a cleansing foam, a cleansing lotion, a cleansing cream, a body lotion, a body cleanser, an emulsion, a lipstick, a makeup base, a foundation, a press powder, a loose powder, an eye shadow, and the like.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another exemplary embodiment of the present invention, a bacterial metagenomic analysis was performed by using vesicles isolated from the blood of normal individuals who were matched in age and sex with patients with gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, and diabetes. As a result, it was confirmed that vesicles derived from bacteria belonging to the genus *Micrococcus* were significantly decreased in clinical samples of patients with gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, and diabetes as compared to samples of normal individuals (see Examples 3 to 15).

In another embodiment of the present invention, it was evaluated whether vesicles secreted from a cultured *Micrococcus luteus* strain exhibit immunomodulatory and anti-inflammatory effects, and as a result of evaluating the secretion of inflammatory mediators by macrophages treated with vesicles derived from *Micrococcus luteus* at various concentrations, followed by treatment with *E. coli*-derived vesicles, which are a causative factor for inflammatory diseases, it was confirmed that the secretion of IL-6 and TNF-α, which was caused by the *E. coli*-derived vesicle, was efficiently inhibited by the vesicles derived from *Micrococcus luteus* (see Example 18).

Hereinafter, preferred Examples for helping the understanding of the present invention will be suggested. However, the following Examples are provided only to more easily understand the present invention, and the contents of the present invention are not limited by the following Examples.

MODES OF THE INVENTION

Examples

Example 1. Analysis of In Vivo Absorption, Distribution, and Excretion Patterns of Intestinal Bacteria and Vesicles Derived from Bacteria In order to evaluate whether intestinal bacteria and vesicles derived from bacteria were systemically absorbed through the gastrointestinal tract, an experiment was performed with the following method. A dose of 50 μg of each of intestinal bacteria and vesicles derived from intestinal bacteria labeled with fluorescence in the stomach of a mouse were administered to the gastrointestinal tract, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration.

In addition, in order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed.

Example 2. Metagenomic Analysis of Vesicles Derived from Bacteria in Clinical Sample A clinical sample such as blood was first put into a 10-ml tube, suspended matter was allowed to settle down by centrifugation (3,500×g, 10 min, 4° C.), and only the supernatant was transferred to a new 10-ml tube. After bacteria and impurities were removed by using a 0.22-μm filter, they were transferred to a CENTRIPREP™ tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
|---|---|---|---|
| 16S rDNA | 16S_V3_F | 5'-TCGTCGGCAGCGTCAGATGTGTATAAGAGACAGCCTACGGGNGGCWGCAG-3' | 1 |
| | 16S_V4_R | 5'-GTCTCGTGGGCTCGGAGATGTGTATAAGAGACAGGACTACHVGGGTATCTAATCC | 2 |

The DNA extracted by the above method was amplified using the 16S rDNA primers, and then sequencing was performed (ILLUMINA MISEQ™ sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the operational taxonomy unit (OTU) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2:
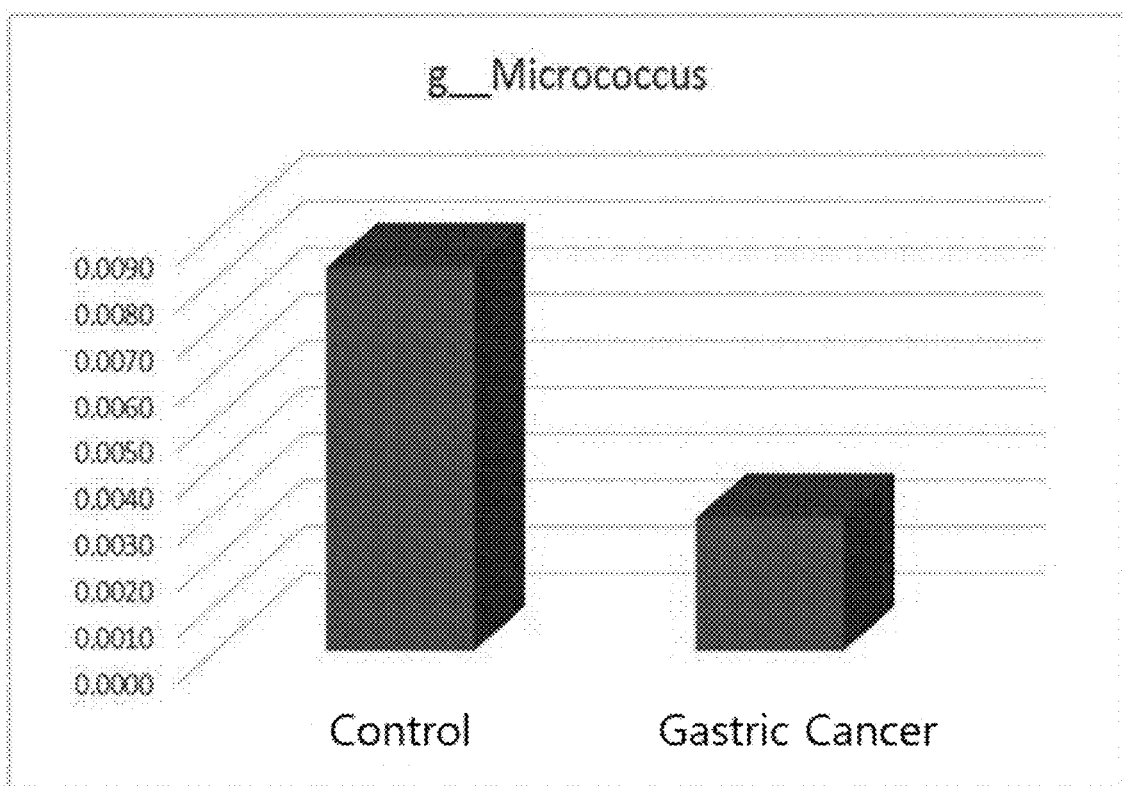
FIG. 2 is a result of comparing the distributions of vesicles derived from bacteria belonging to the genus *Micrococcus* after metagenomic analysis of bacteria-derived vesicles present in the blood of gastric cancer patients and a normal individuals.

Example 3. Metagenomic Analysis of Vesicles Derived from Bacteria in Blood of Patient with Gastric Cancer Genes were extracted from vesicles present in blood samples of 66 gastric cancer patients and 198 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with gastric cancer as compared to the blood from the normal individuals (see Table 2 and FIG. 2).

TABLE 2

| Blood | Control | | Gasric Cancer | | t-test | |
|---|---|---|---|---|---|---|
| Taxon | Mean | SD | Mean | SD | p-value | Ratio |
| g_*Micrococcus* | 0.0083 | 0.0115 | 0.0029 | 0.0051 | <0.0001 | 0.35 |

Figure 3:
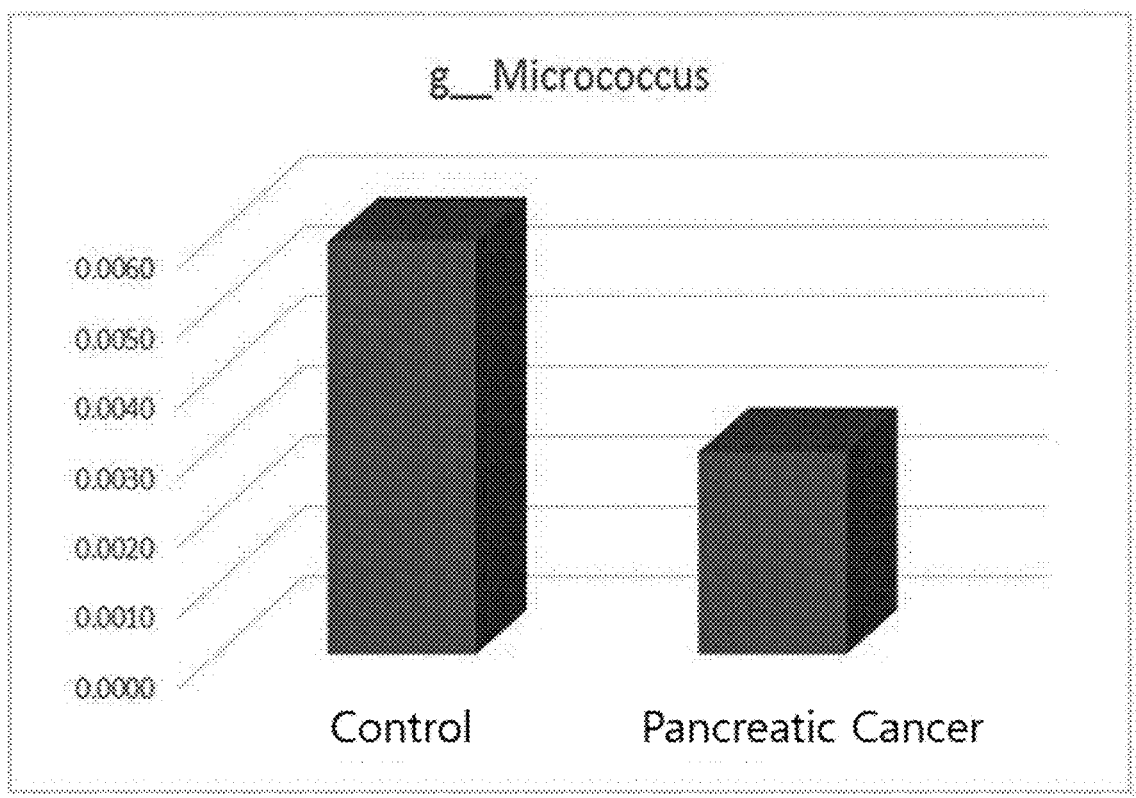
FIG. 3 is a result of comparing the distributions of vesicles derived from bacteria belonging to the genus *Micrococcus* after metagenomic analysis of bacteria-derived vesicles present in the blood of pancreatic cancer patients and a normal individuals.

Example 4. Metagenomic Analysis of Vesicles Derived from Bacteria in Blood of Patient with Pancreatic Cancer Genes were extracted from vesicles present in blood samples of 176 pancreatic cancer patients and 271 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with pancreatic cancer as compared to the blood from the normal individuals (see Table 3 and FIG. 3).

TABLE 3

| Blood | Control | | Pancreatic Cancer | | t-test | |
|---|---|---|---|---|---|---|
| Taxon | Mean | SD | Mean | SD | p-value | Ratio |
| g_*Micrococcus* | 0.0059 | 0.0101 | 0.0029 | 0.0042 | <0.0001 | 0.49 |

Figure 4:
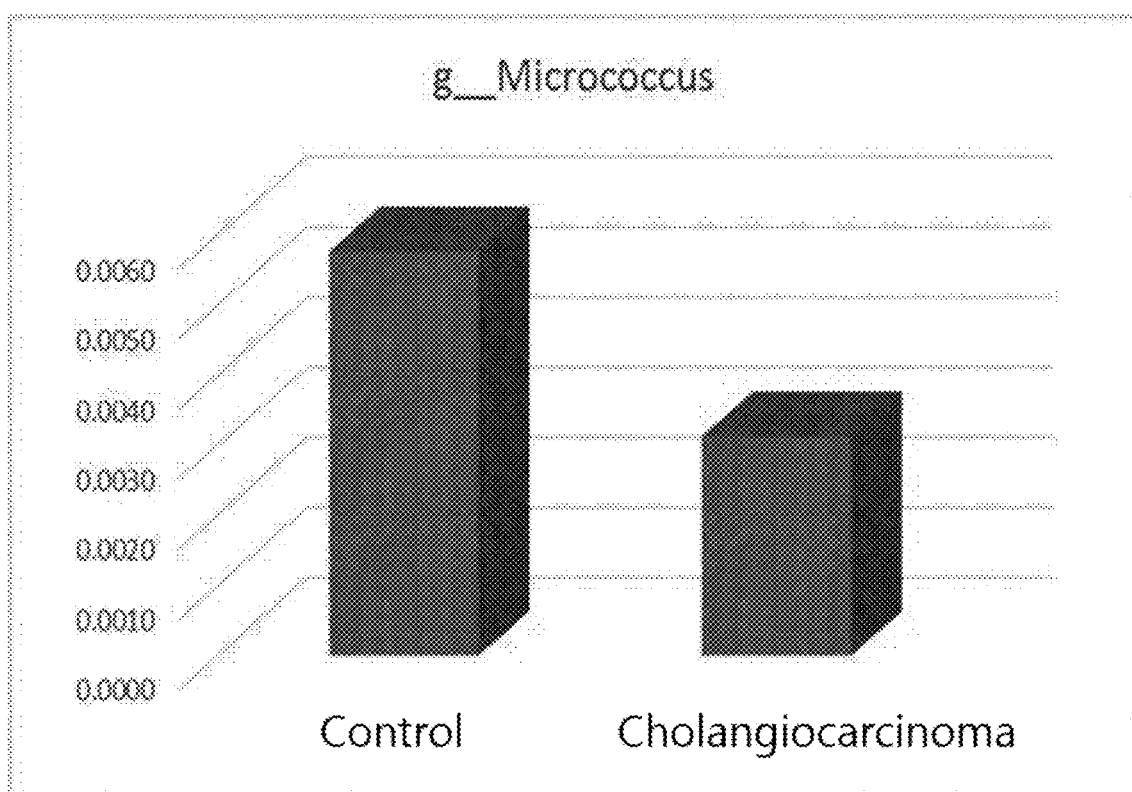
FIG. 4 is a result of comparing the distributions of vesicles derived from bacteria belonging to the genus *Micrococcus* after metagenomic analysis of bacteria-derived vesicles present in the blood of cholangiocarcinoma patients and a normal individuals.

Example 5. Metagenomic Analysis of Vesicles Derived from Bacteria in Blood of Patient with Cholangiocarcinoma Genes were extracted from vesicles present in blood samples of 79 cholangiocarcinoma patients and 259 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with cholangiocarcinoma as compared to the blood from the normal individuals (see Table 4 and FIG. 4).

TABLE 4

| Blood | Control | | Cholangiocarcinoma | | t-test | |
|---|---|---|---|---|---|---|
| Taxon | Mean | SD | Mean | SD | p-value | Ratio |
| g_*Micrococcus* | 0.0058 | 0.0101 | 0.0031 | 0.0107 | 0.04 | 0.54 |

Figure 5:
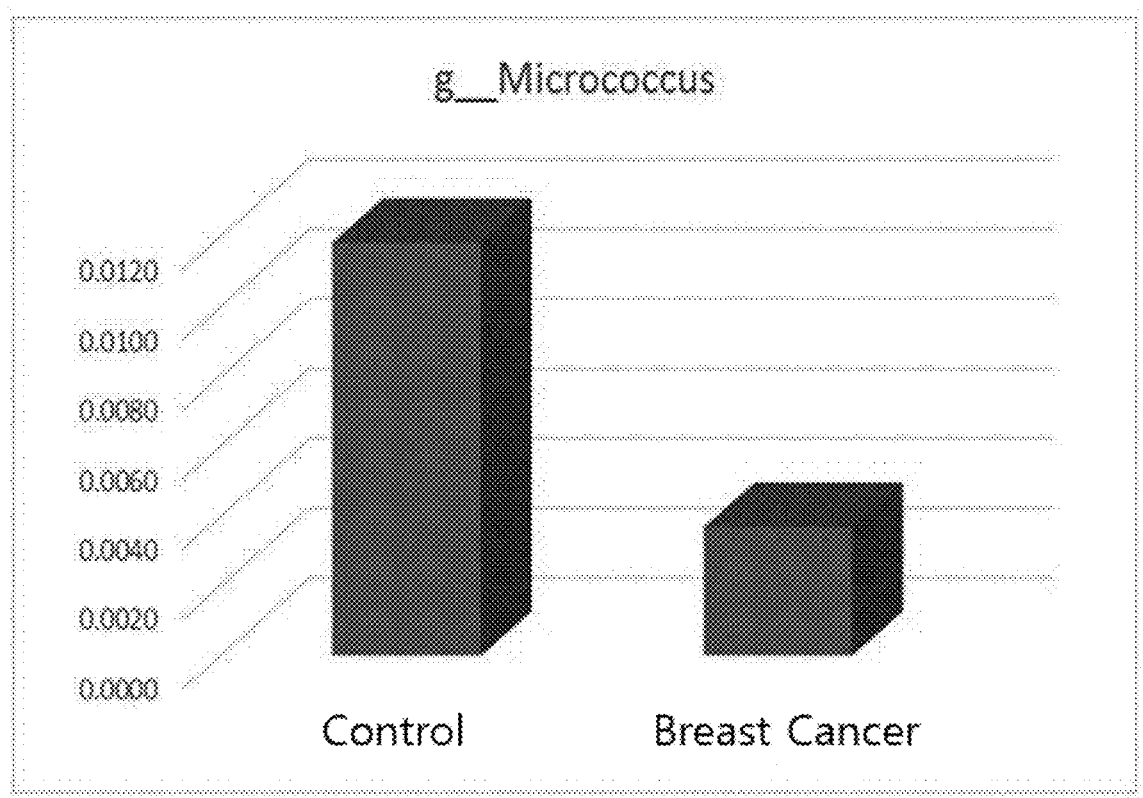
FIG. 5 is a result of comparing the distributions of vesicles derived from bacteria belonging to the genus *Micrococcus* after metagenomic analysis of bacteria-derived vesicles present in the blood of breast cancer patients and a normal individuals.

Example 6. Metagenomic Analysis of Vesicles Derived from Bacteria in Blood of Patient with Breast Cancer Genes were extracted from vesicles present in blood samples of 96 breast cancer patients and 192 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with breast cancer as compared to the blood from the normal individuals (see Table 5 and FIG. 5).

TABLE 5

| Blood | Control | | Breast Cancer | | t-test | |
|---|---|---|---|---|---|---|
| Taxon | Mean | SD | Mean | SD | p-value | Ratio |
| g_*Micrococcus* | 0.0118 | 0.0164 | 0.0037 | 0.0061 | <0.0001 | 0.31 |

Figure 6:
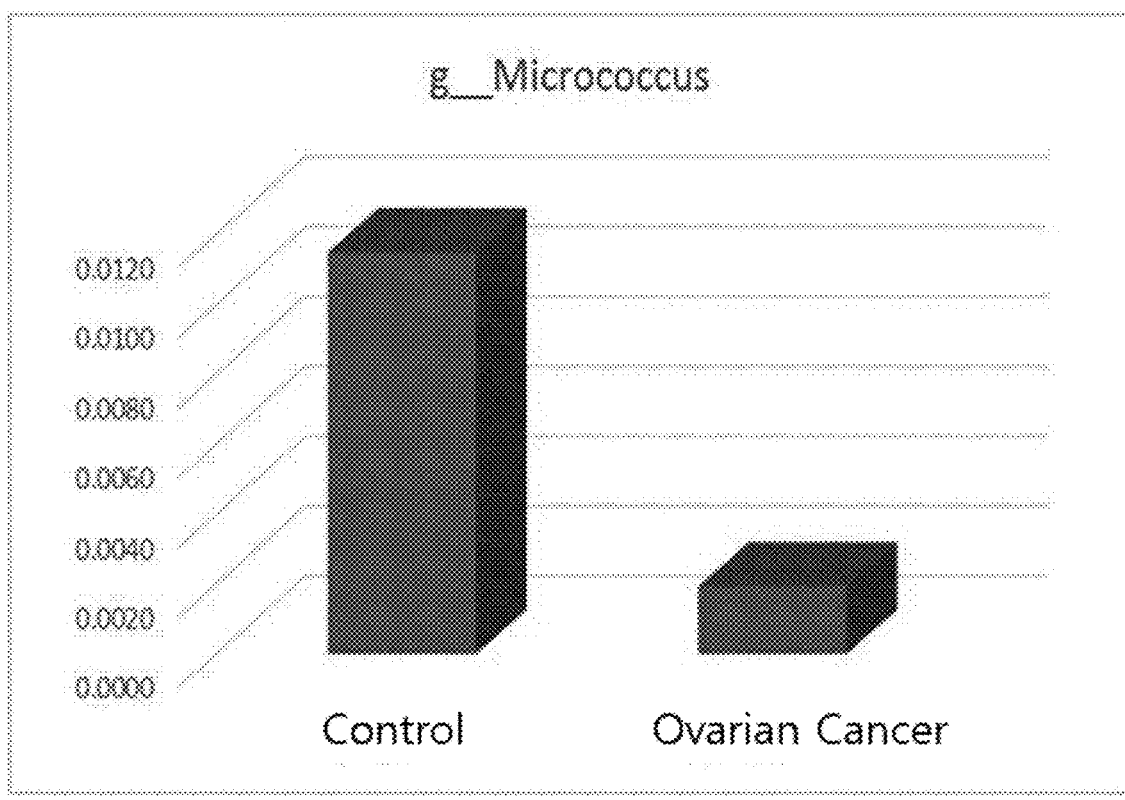
FIG. 6 is a result of comparing the distributions of vesicles derived from bacteria belonging to the genus *Micrococcus* after metagenomic analysis of bacteria-derived vesicles present in the blood of ovarian cancer patients and a normal individuals.

Example 7. Metagenomic Analysis of Vesicles Derived from Bacteria in Blood of Patient with Ovarian Cancer Genes were extracted from vesicles present in blood samples of 137 ovarian cancer patients and 139 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with ovarian cancer as compared to the blood from the normal individuals (see Table 6 and FIG. 6).

TABLE 6

| Blood | Control | | Ovarian Cancer | | t-test | |
|---|---|---|---|---|---|---|
| Taxon | Mean | SD | Mean | SD | p-value | Ratio |
| g_*Micrococcus* | 0.0115 | 0.0185 | 0.0019 | 0.0034 | <0.0001 | 0.17 |

Figure 7:
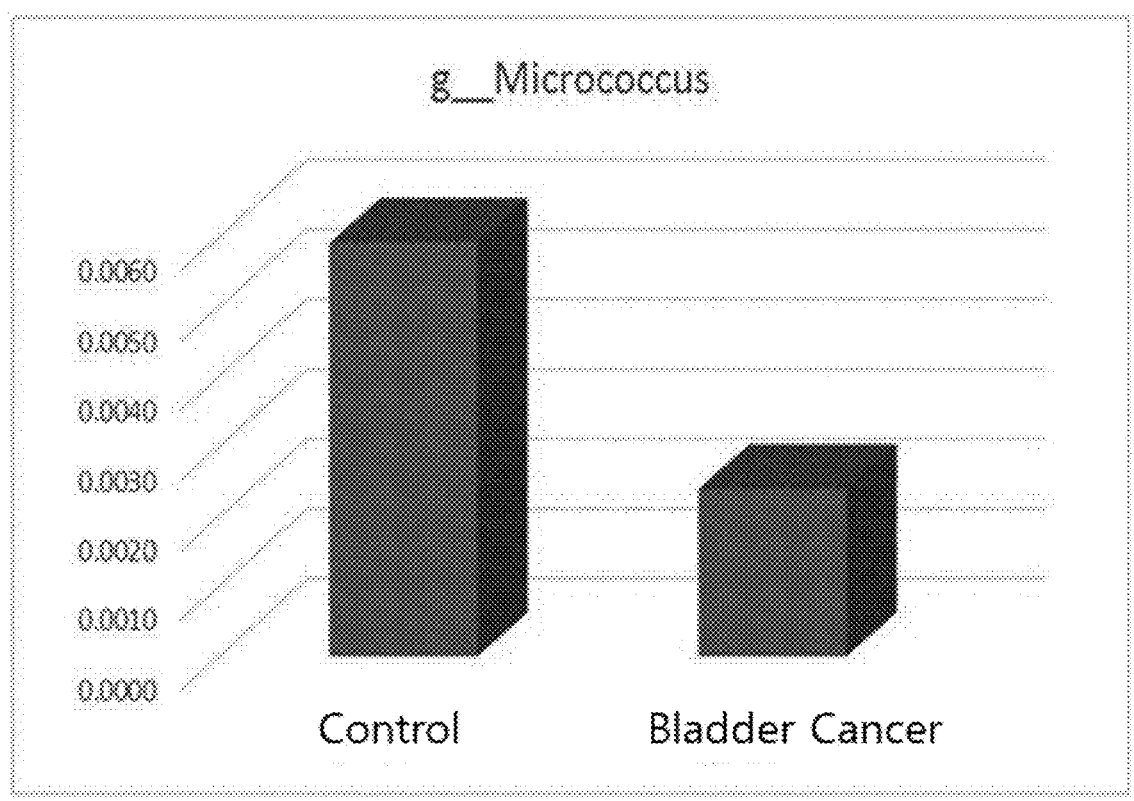
FIG. 7 is a result of comparing the distributions of vesicles derived from bacteria belonging to the genus *Micrococcus* after metagenomic analysis of bacteria-derived vesicles present in the blood of bladder cancer patients and a normal individuals.

Example 8. Metagenomic Analysis of Vesicles Derived from Bacteria in Blood of Patient with Bladder Cancer Genes were extracted from vesicles present in blood samples of 91 bladder cancer patients and 176 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with bladder cancer as compared to the blood from the normal individuals (see Table 7 and FIG. 7).

TABLE 7

| Blood | Control | | Bladder Cancer | | t-test | |
|---|---|---|---|---|---|---|
| Taxon | Mean | SD | Mean | SD | p-value | Ratio |
| g_*Micrococcus* | 0.0059 | 0.0120 | 0.0024 | 0.0024 | 0.0006 | 0.41 |

Figure 8:
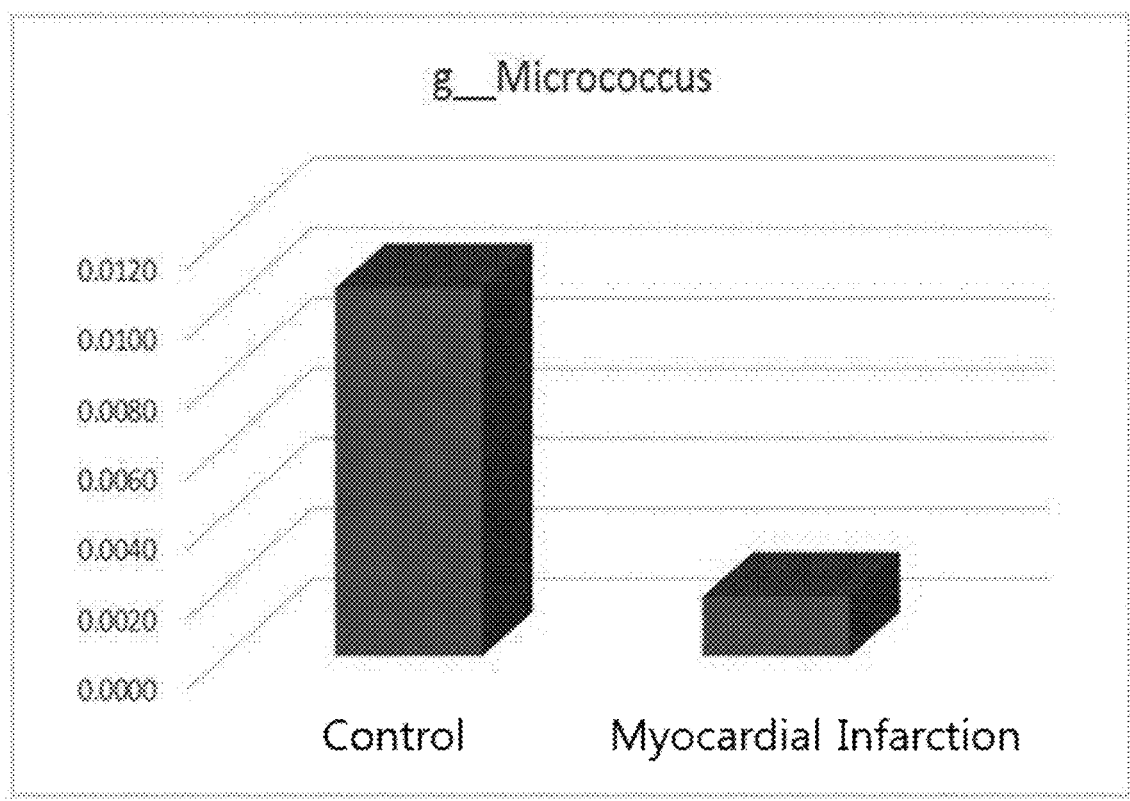
FIG. 8 is a result of comparing the distributions of vesicles derived from bacteria belonging to the genus *Micrococcus* after metagenomic analysis of bacteria-derived vesicles present in the blood of myocardial infarction patients and a normal individuals.

Example 9. Metagenomic Analysis of Vesicles Derived from Bacteria in Blood of Patient with Myocardial Infarction Genes were extracted from vesicles present in blood samples of 57 myocardial infarction patients and 163 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with myocardial infarction as compared to the blood from the normal individuals (see Table 8 and FIG. 8).

TABLE 8

| Blood | Control | | Myocardial Infarction | | t-test | |
|---|---|---|---|---|---|---|
| Taxon | Mean | SD | Mean | SD | p-value | Ratio |
| g_*Micrococcus* | 0.0105 | 0.0165 | 0.0017 | 0.0043 | <0.0001 | 0.16 |

Figure 9:
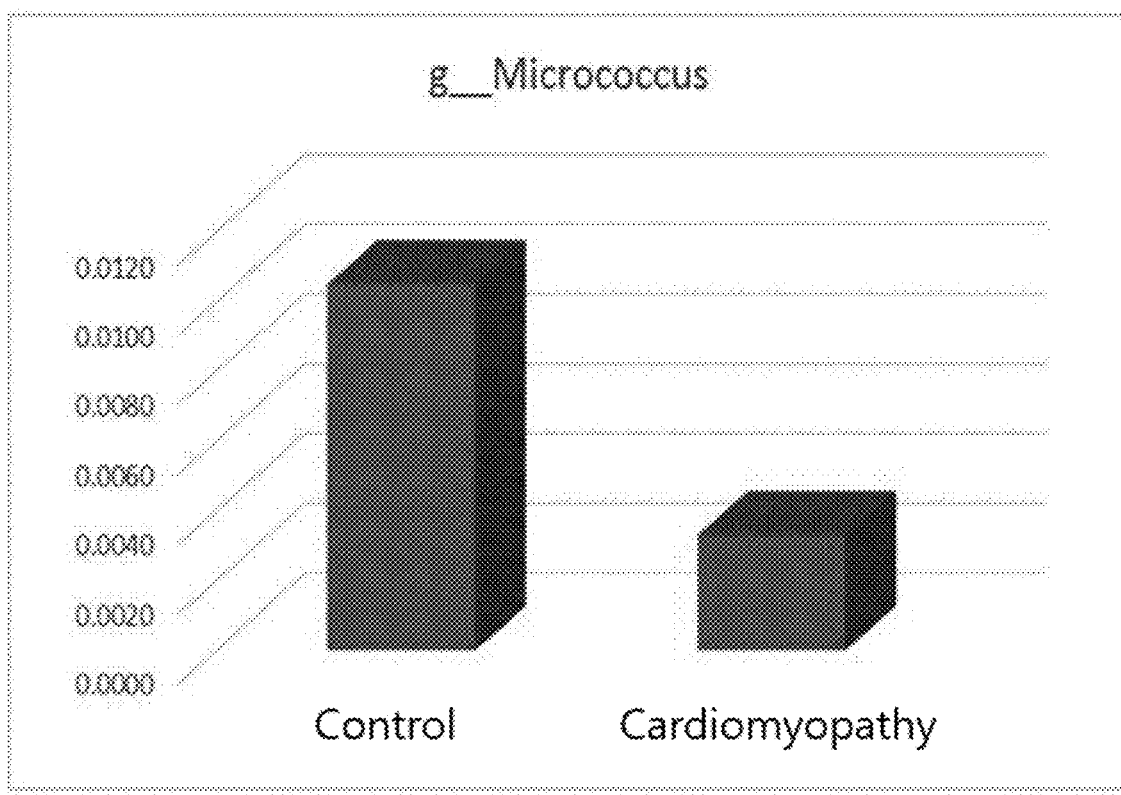
FIG. 9 is a result of comparing the distributions of vesicles derived from bacteria belonging to the genus *Micrococcus* after metagenomic analysis of bacteria-derived vesicles present in the blood of cardiomyopathy patients and a normal individuals.

Example 10. Metagenomic Analysis of Vesicles Derived from Bacteria in Blood of Patient with Cardiomyopathy Genes were extracted from vesicles present in blood samples of 72 cardiomyopathy patients and 163 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with cardiomyopathy as compared to the blood from the normal individuals (see Table 9 and FIG. 9).

TABLE 9

| Blood | Control | | Cardiomyopathy | | t-test | |
|---|---|---|---|---|---|---|
| Taxon | Mean | SD | Mean | SD | p-value | Ratio |
| g_*Micrococcus* | 0.0105 | 0.0165 | 0.0033 | 0.0052 | <0.0001 | 0.32 |

Figure 10:
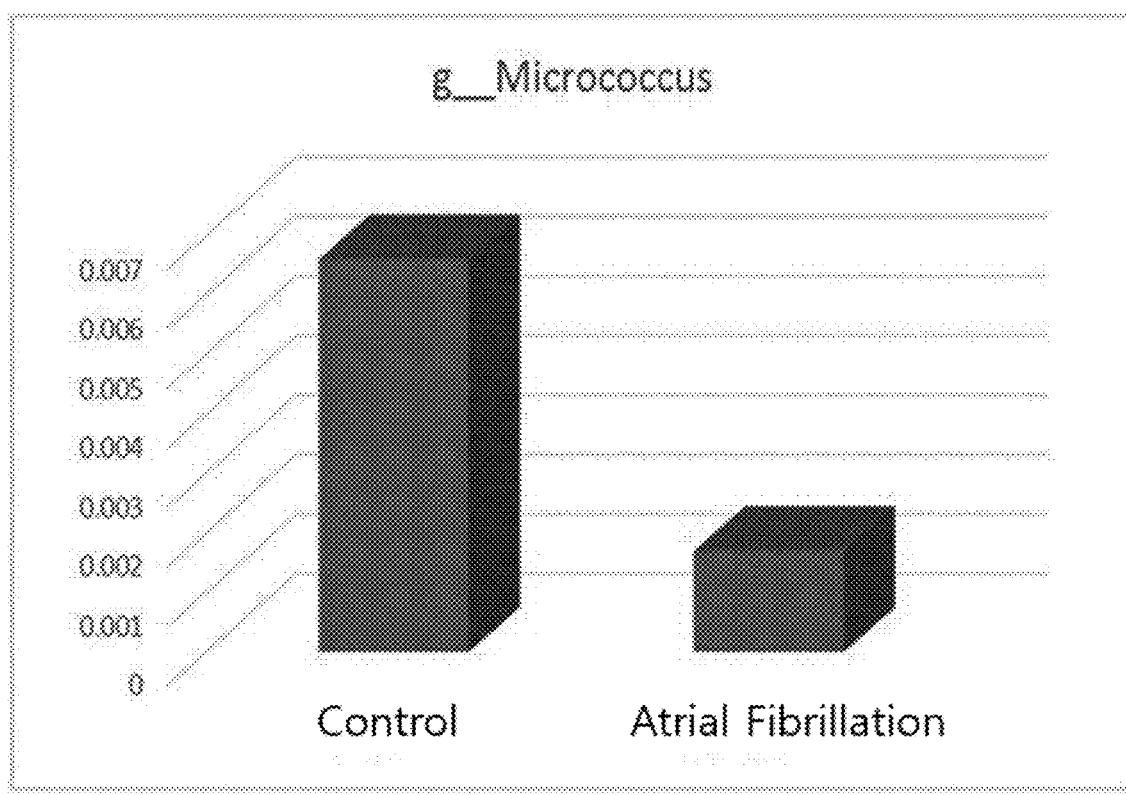
FIG. 10 is a result of comparing the distributions of vesicles derived from bacteria belonging to the genus *Micrococcus* after metagenomic analysis of bacteria-derived vesicles present in the blood of atrial fibrillation patients and a normal individuals.

Example 11. Metagenomic Analysis of Vesicles Derived from Bacteria in Blood of Patient with Atrial Fibrillation Genes were extracted from vesicles present in blood samples of 34 atrial fibrillation patients and 62 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with atrial fibrillation as compared to the blood from the normal individuals (see Table 10 and FIG. 10).

TABLE 10

| Blood | Control | | Atrial Fibrillation | | t-test | |
|---|---|---|---|---|---|---|
| Taxon | Mean | SD | Mean | SD | p-value | Ratio |
| g_*Micrococcus* | 0.0066 | 0.0113 | 0.0017 | 0.0016 | 0.001 | 0.26 |

Figure 11:
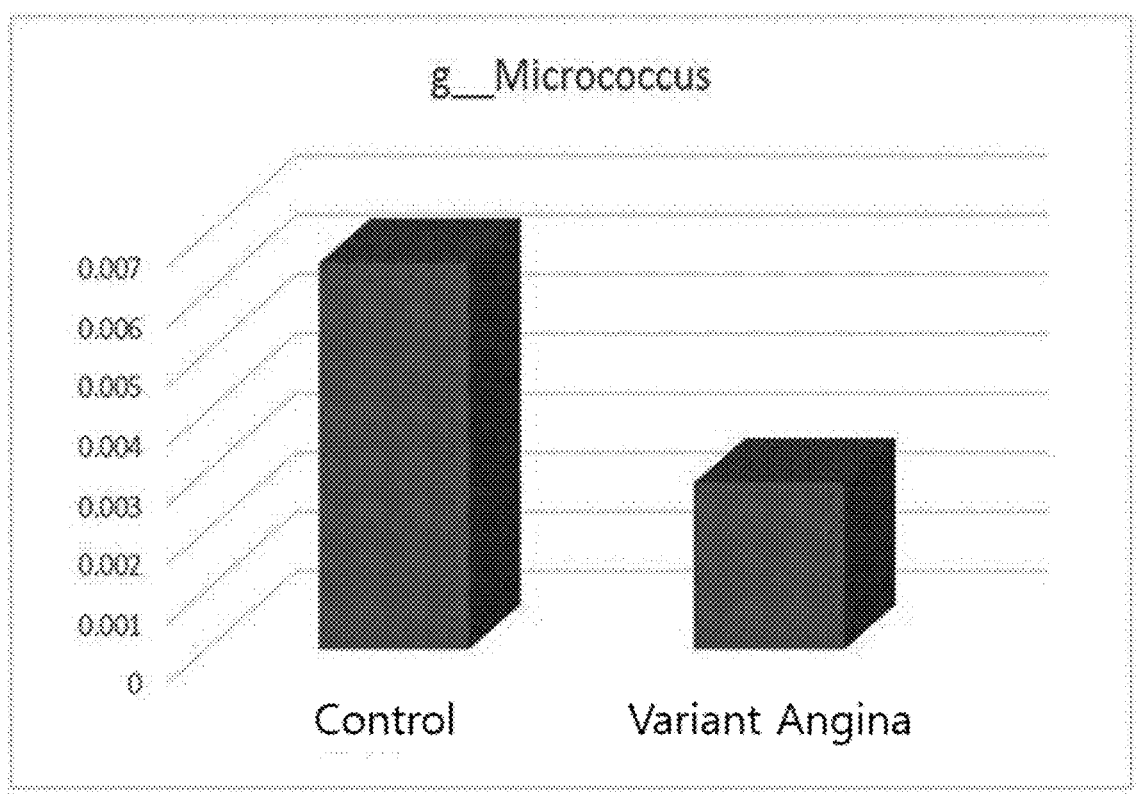
FIG. 11 is a result of comparing the distributions of vesicles derived from bacteria belonging to the genus *Micrococcus* after metagenomic analysis of bacteria-derived vesicles present in the blood of variant angina patients and a normal individuals.

Example 12. Metagenomic Analysis of Vesicles Derived from Bacteria in Blood of Patient with Variant Angina Genes were extracted from vesicles present in blood samples of 80 variant angina patients and 80 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with variant angina as compared to the blood from the normal individuals (see Table 11 and FIG. 11).

TABLE 11

| Blood | Control | | Variant Angina | | t-test | |
|---|---|---|---|---|---|---|
| Taxon | Mean | SD | Mean | SD | p-value | Ratio |
| g_*Micrococcus* | 0.0065 | 0.0151 | 0.0028 | 0.0045 | 0.03 | 0.43 |

Figure 12:
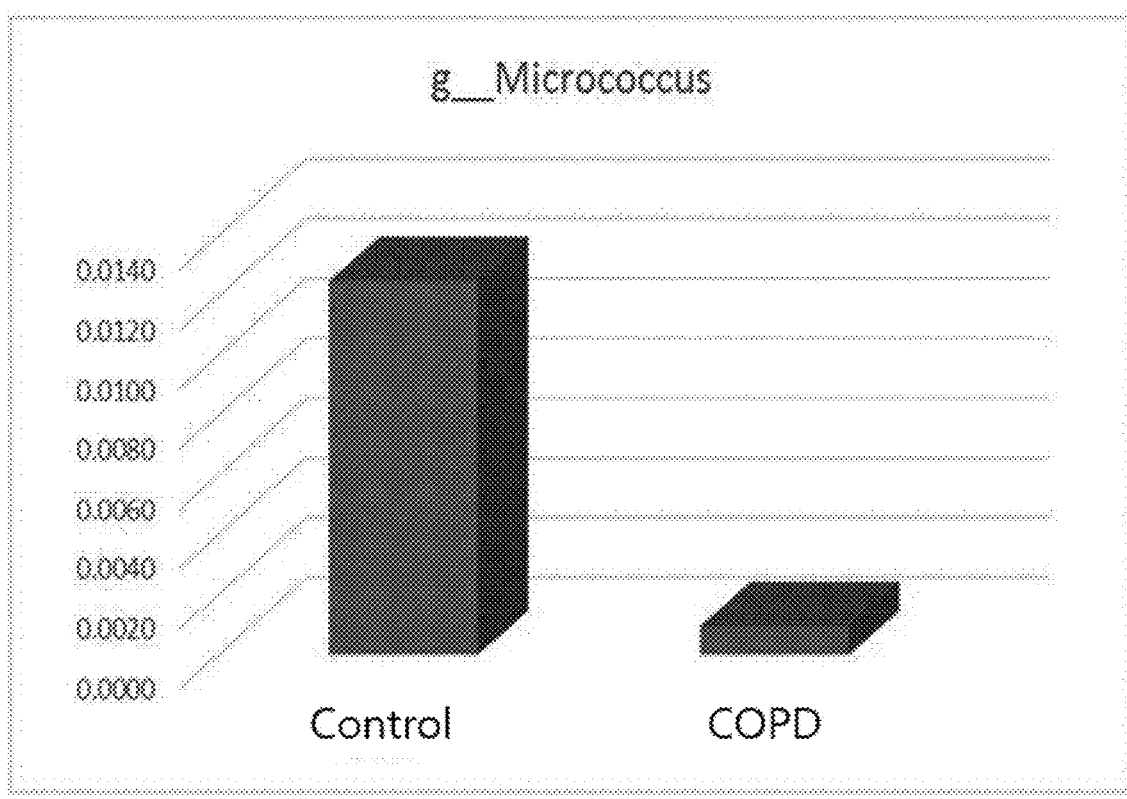
FIG. 12 is a result of comparing the distributions of vesicles derived from bacteria belonging to the genus *Micrococcus* after metagenomic analysis of bacteria-derived vesicles present in the blood of chronic obstructive pulmonary disease (COPD) patients and a normal individuals.

Example 13. Metagenomic Analysis of Vesicles Derived from Bacteria in Blood of Patient with COPD Genes were extracted from vesicles present in blood samples of 205 COPD patients and 231 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with COPD as compared to the blood from the normal individuals (see Table 12 and FIG. 12).

TABLE 12

| Blood | Control | | COPD | | t-test | |
|---|---|---|---|---|---|---|
| Taxon | Mean | SD | Mean | SD | p-value | Ratio |
| g_*Micrococcus* | 0.0125 | 0.0121 | 0.0010 | 0.0017 | <0.0001 | 0.08 |

Figure 13:
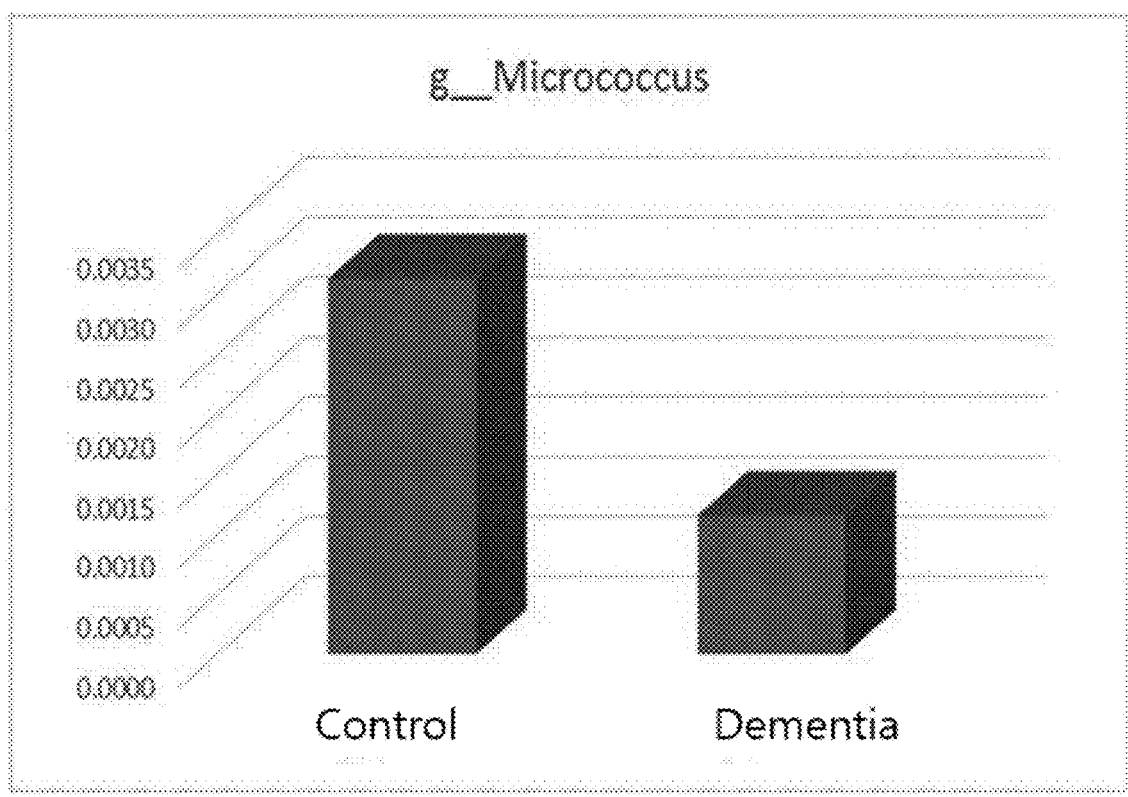
FIG. 13 is a result of comparing the distributions of vesicles derived from bacteria belonging to the genus *Micrococcus* after metagenomic analysis of bacteria-derived vesicles present in the blood of dementia patients and a normal individuals.

Example 14. Metagenomic Analysis of Vesicles Derived from Bacteria in Blood of Patient with Dementia Genes were extracted from vesicles present in blood samples of 67 dementia patients and 70 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with dementia as compared to the blood from the normal individuals (see Table 13 and FIG. 13).

TABLE 13

| Blood | Control | | dementia | | t-test | |
|---|---|---|---|---|---|---|
| Taxon | Mean | SD | Mean | SD | p-value | Ratio |
| g_*Micrococcus* | 0.0031 | 0.0087 | 0.0012 | 0.0027 | 0.0003 | 0.36 |

Figure 14:
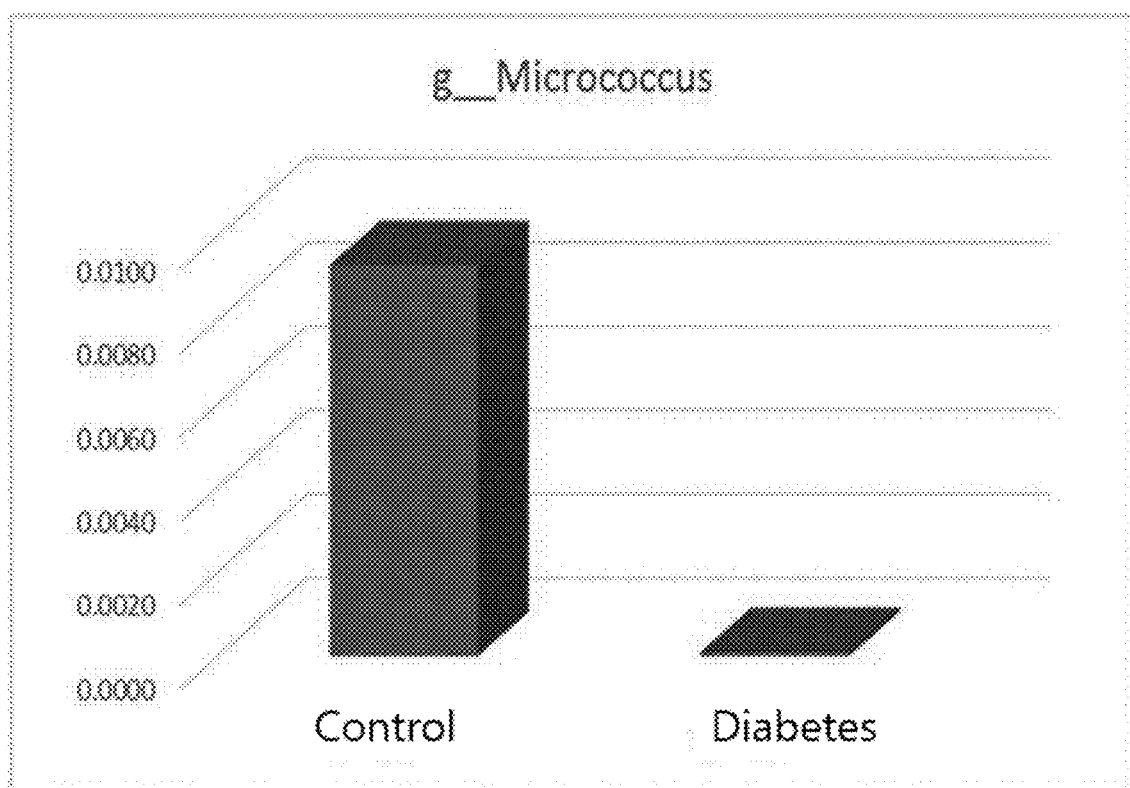
FIG. 14 is a result of comparing the distributions of vesicles derived from bacteria belonging to the genus *Micrococcus* after metagenomic analysis of bacteria-derived vesicles present in the blood of diabetes patients and a normal individuals.

Example 15. Metagenomic Analysis of Vesicles Derived from Blood, Urine, and Saliva Bacteria of Patient with Diabetes Genes were extracted from vesicles present in blood samples of 61 diabetes patients and 122 normal individuals, the two groups matched in age and gender, metagenomic analysis was performed thereon using the method of Example 2, and then the distribution of vesicles derived from bacteria belonging to the genus *Micrococcus* was evaluated. As a result, it was confirmed that vesicles derived from belonging to the genus *Micrococcus* were significantly decreased in the blood from the patients with diabetes as compared to the blood from the normal individuals (see Table 14 and FIG. 14).

TABLE 14

| Blood | Control | | diabetes | | t-test | |
|---|---|---|---|---|---|---|
| Taxon | Mean | SD | Mean | SD | p-value | Ratio |
| g_*Micrococcus* | 0.0093 | 0.0154 | 0.0001 | 0.0001 | <0.0001 | 0.01 |

Example 16. Isolation of Vesicles from *Micrococcus luteus* Culturing Solution

Based on the above examples, an *M. luteus* strain was cultured, and then vesicles were isolated therefrom and characteristics of the isolated vesicles were analyzed. The strain *M. luteus* was cultured in a MRS (de Man-Rogosa and Sharpe) medium in an aerobic chamber at 37° C. until absorbance ($OD_{600}$) reached 1.0 to 1.5, and then sub-cultured. Subsequently, a culture supernatant including the strain was recovered and centrifuged at 10,000 g and 4° C. for 20 minutes, and then the strain was removed and filtered through a 0.22 μm filter. The filtered supernatant was concentrated to a volume of 50 ml through microfiltration by using a MASTERFLEX™ pump system (Cole-Parmer, US) with a 100 kDa PELLICON™ 2 Cassette filter membrane (Merck Millipore, US). The concentrated supernatant was filtered once again with a 0.22-μm filter. Thereafter, proteins were quantified by using a BCA assay, and the following experiments were performed on the obtained vesicles.

Example 17. Inflammation-Inducing Effect of *M. luteus*-Derived Vesicles

To examine an effect of *M. luteus*-derived vesicles on the secretion of inflammatory mediators (IL-6 and TNF-α) in inflammatory cells, Raw 264.7 cells, which is a mouse macrophage line, were treated with *M. luteus*-derived vesicles at various concentrations (0.1, 1, or 10 μg/ml), followed by ELISA.

More specifically, Raw 264.7 cells, which were dispensed into a 48-well cell culture plate at a density of $4 \times 10^4$ cells/well, were treated with various concentrations of *M. luteus*-derived vesicles in a Dulbecco's Modified Eagle's Medium (DMEM) serum-free medium and cultured for 12 hours. Subsequently, the cell culture solution was collected in a 1.5 ml tube and centrifuged at 3,000×g for 5 minutes, and the supernatant was collected and stored at −80° C., followed by ELISA.

For ELISA, a capture antibody was diluted with phosphate buffered saline (PBS) and 50 μl aliquots thereof were dispensed into a 96-well polystyrene plate in accordance with a working concentration, and then allowed to react at 4° C. overnight. Subsequently, the sample was washed three times with 100 μl of a PBST (0.05% TWEEN™-20-containing PBS) solution, and then an RD (1% bovine serum albumin (BSA)-containing PBS) solution was dispensed in 100 μl aliquots, followed by blocking at room temperature for 1 hour, and then the sample and a standard were dispensed in 50 µl aliquots in accordance with concentration and allowed to react at room temperature for 2 hours. Then, the sample and the standard were washed three times with 100 µl of PBST, and then the detection antibody was diluted with RD, and the diluted solution was dispensed in 50 µl aliquots in accordance with a working concentration and allowed to react at room temperature for 2 hours.

Thereafter, the sample and the standard were washed three times with 100 µl of PBST, and then streptavidin-horseradish peroxidase (HRP) (R&D Systems, USA) was diluted in RD to 1/40, and the diluted solution was dispensed in 50 µl aliquots and allowed to react at room temperature for 20 minutes. Lastly, the sample and the standard were washed three times with 100 µl of PBST, and then a tetramethylbenzidine (TMB) substrate (SurModics, USA) was dispensed in 50 µl aliquots, and then when color was developed after 5 minutes to 20 minutes, a 1M sulfuric acid solution was dispensed in 50 µl aliquots, thereby stopping the reaction, and absorbance at 450 nm was measured using a SPECTRAMAX™ M3 microplate reader (Molecular Devices, USA).

Figure 15:
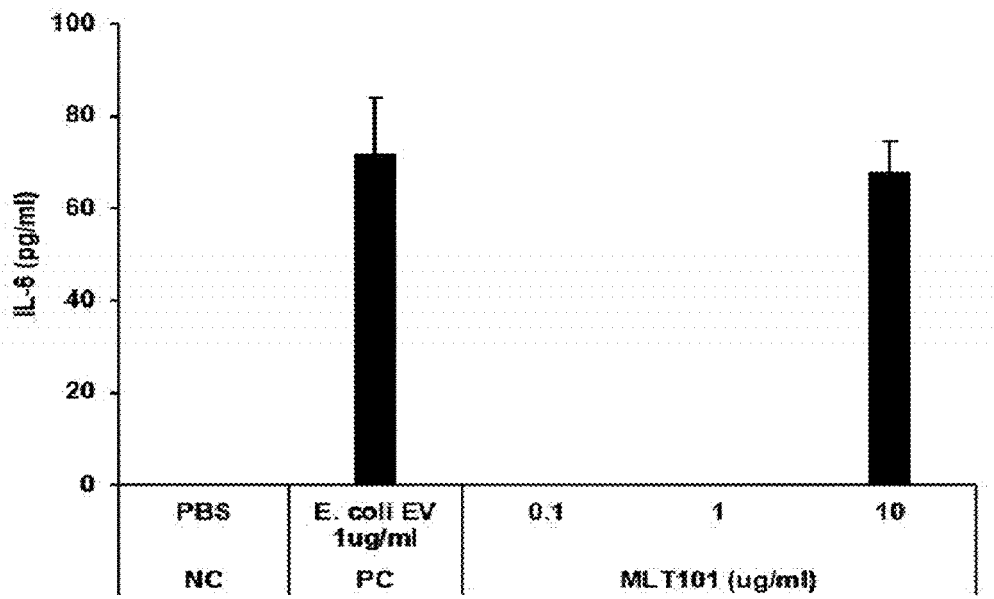
FIG. 15 illustrates results of comparing the degree of secretion of IL-6 and TNF-α, which are inflammatory mediators, between macrophages (Raw264.7 cells) treated with vesicles derived from *Micrococcus* luteus and *E. coli* EVs, which are pathogenic vesicles, to evaluate an effect of vesicles derived from *Micrococcus luteus* on inducing inflammation.
Figure 15:
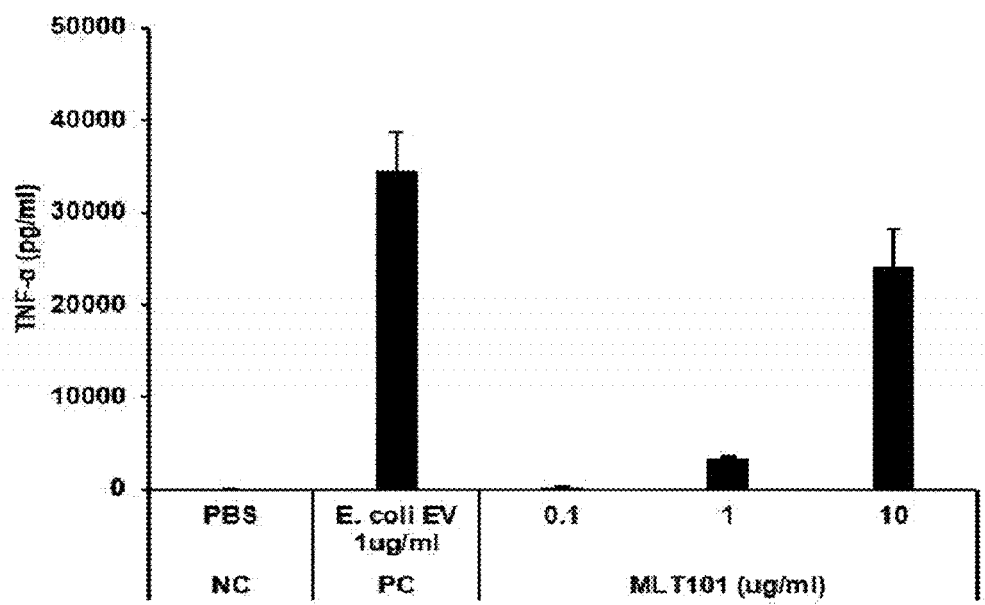

As a result, as illustrated in FIG. 15, it was confirmed that the secretion of inflammatory mediators was significantly reduced when macrophages were treated with *M. luteus*-derived vesicles, compared to *E. coli* EVs, which are pathogenic vesicles.

Example 18. Anti-inflammatory Effects of Vesicles Derived from *Micrococcus luteus*

Based on result of the above example 17, in order to investigate the effects of vesicles derived from *Micrococcus luteus* on the secretion of inflammatory mediators in inflammatory cells, after Raw 264.7 cells which are mouse macrophages were treated with vesicles derived from *Micrococcus luteus* at various concentrations (0.1, 1, 10 µg/ml), the amount of inflammatory mediators (IL-6, TNf-α, and the like) secreted was measured by treating vesicles derived from *Escherichia coli* (*E. coli* EV) which are vesicles for inflammatory disease pathogenesis. More specifically, after Raw 264.7 cells were aliquoted at $1 \times 10^5$ cells/well into a 24-well cell culture plate, the cells were cultured in a DMEM complete medium for 24 hours. Thereafter, the culture supernatant was collected in a 1.5-ml tube and centrifuged at 3,000 g for 5 minutes, the supernatant was recovered and stored at 4° C., and then an ELISA analysis was performed. As a result, as illustrated in FIG. 16, it was confirmed that when the vesicles derived from *Micrococcus luteus* were pre-treated, the secretion of IL-6 and TNF-α by the vesicles derived from *Escherichia coli* was remarkably suppressed. These results indicate that vesicles derived from *Micrococcus luteus* are capable of effectively inhibiting inflammatory responses induced by pathogenic vesicles such as *E. coli*-derived EVs.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Vesicles derived from bacteria belonging to the genus *Micrococcus* according to the present invention can be used not only in a method of diagnosing gastric cancer, pancreatic cancer, cholangiocarcinoma, breast cancer, ovarian cancer, bladder cancer, myocardial infarction, cardiomyopathy, atrial fibrillation, variant angina, chronic obstructive pulmonary disease (COPD), dementia, or diabetes, but also as a composition for preventing, alleviating, or treating the above-described diseases, and thus are expected to be effectively used in the related medical, cosmetic, and food industrial fields.

The invention claimed is:

1. A method of suppressing inflammation in a mammal, the method comprising treating the mammal by administering a composition comprising an effective amount of extracellular vesicles isolated from *Micrococcus luteus* and measuring the suppression of inflammation.

2. The method of claim 1, wherein the composition is a pharmaceutical composition, or a food composition.

3. The method of claim 1, wherein the vesicles have an average diameter of 10 to 200 nm.

4. The method of claim 1, wherein the vesicles are naturally secreted or artificially isolated from the *Micrococcus luteus*.

5. The method of claim 1, wherein the composition is an inhalant composition.

6. The method of claim 1, wherein the suppression of inflammation is determined by inhibited secretion of IL-6 and TNF-alpha inflammatory mediators.

* * * * *